US00PP17155P3

(12) United States Plant Patent
Olbricht

(10) Patent No.: US PP17,155 P3
(45) Date of Patent: Oct. 17, 2006

(54) **VARIETY OF *ANGELONIA* PLANT NAMED 'ANSKY'**

(50) Latin Name: ***Angelonia* hybrid**
Varietal Denomination: Ansky

(75) Inventor: Klaus Olbricht, Dresden (DE)

(73) Assignee: Elsner pac Jungpflanzen, Dresden (DE)

( * ) Notice: Subject to any disclaimer, the term of this patent is extended or adjusted under 35 U.S.C. 154(b) by 239 days.

(21) Appl. No.: 11/059,225

(22) Filed: Feb. 16, 2005

(65) Prior Publication Data

US 2006/0185044 P1 Aug. 17, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—The Webb Law Firm

(57) ABSTRACT

A new and distinct flowering *Angelonia* plant with dark leaves and light to medium blue flowers having a whitish edge.

1 Drawing Sheet

Botanical classification: *Angelonia* hybrid.
Varietal Denomination: 'Ansky'.

BACKGROUND OF THE INVENTION

The present invention comprises a new and distinct cultivar of *Angelonia* hybrid known by the varietal name 'Ansky'. The new variety was discovered in a selected breeding program in Dresden, Germany. The new variety is the result of a cross combination breeding between a bulk of unnamed and unpatented medium to light blue genotype selections from a collection of proprietary breeding plants (Group 1K-125). The purpose of the breeding program was to find a new variety with large light blue flowers. The new variety was first asexually reproduced in 2002 by cuttings in Dresden, Germany. The new variety has been trial and field tested in Dresden and has been found to retain its distinctive characteristics and remain true to type through successive propagations. Characteristics distinguishable from other varieties include:

Upright plant habit

Large flowers

Light to medium blue flower color with a whitish edge

Dark green, glossy leaves

DESCRIPTION OF THE DRAWING

The accompanying photographic drawing illustrates the new variety, with the color being as nearly true as is possible with color illustrations of this type.

DESCRIPTION OF THE PLANT

Figure 1:
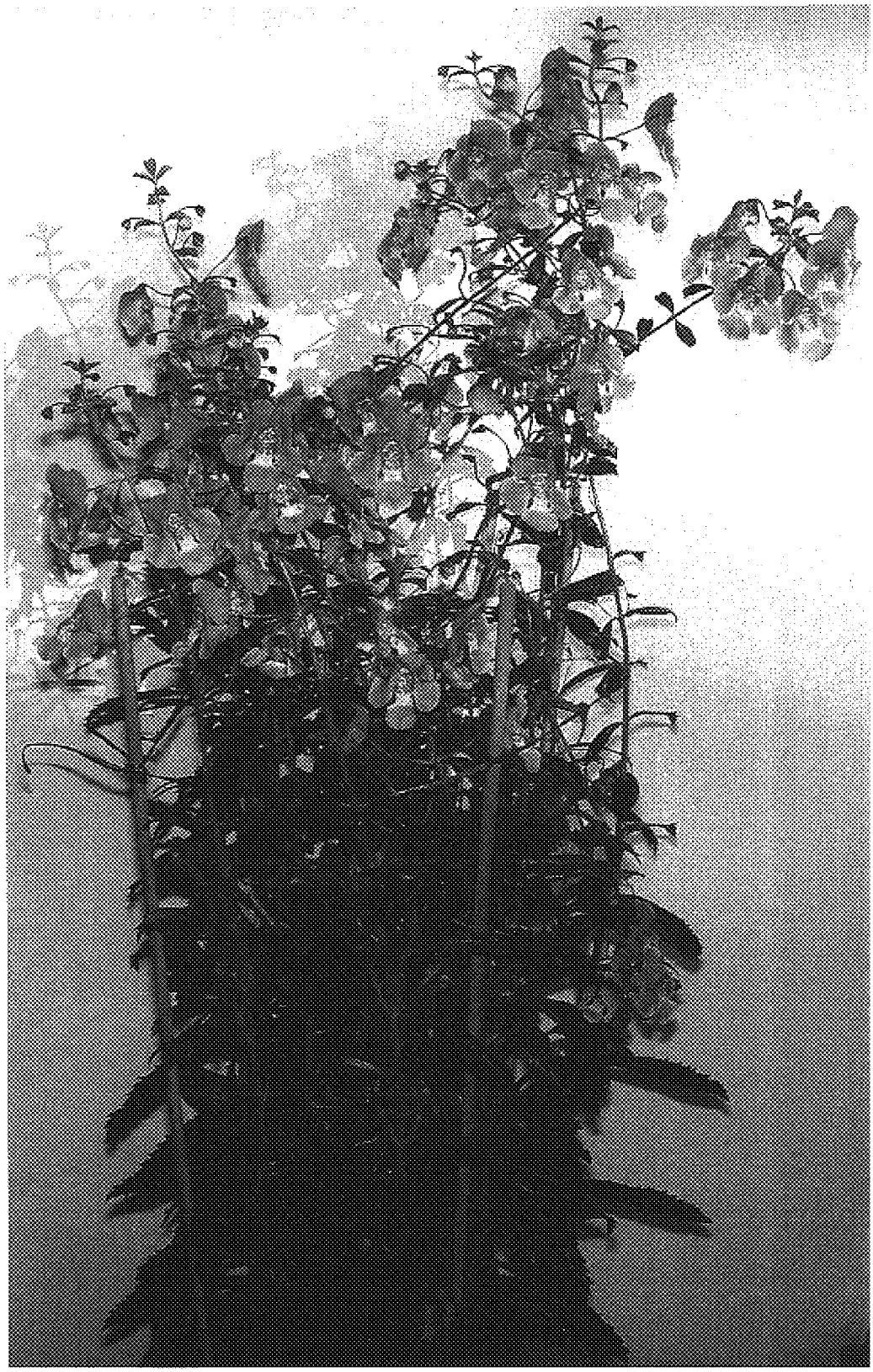

The following detailed description sets forth the characteristics of the new cultivar. The data that defines these characteristics were collected by asexual reproductions carried out in a warm greenhouse in Dresden, Germany. The color readings were taken on a plant indoors under natural light. The new variety was six months old when described.

Color references are primarily to The R.H.S. Colour Chart of The Royal Horticultural Society of London.

PLANT

Form: Upright.
Height: 60 cm from soil to top of foliage and racemose.
Diameter: 30 cm.
Growth: Erect, well-branched, and vigorous.
Time to initiate roots: About 10 days at 22° C.
Time to develop roots: About 30 days at 22° C.
Container size: 19 cm.
Main stem:
- *Form.*—Upright.
- *Color.*—144B.
- *Texture.*—Hairy, sticky.
- *Length.*—Approximately 50 cm.
- *Diameter.*—4–5 mm.
- *Internode length.*—2–4 cm.

Foliage:
- *Arrangement (e.g., alternate, single).*—Opposite, decussate.
- *Number of leaves per branch.*—Many.
- *Size of leaf.*—Length: 4–8 cm. Width: 1.5–2 cm.
- *Shape of leaf (generally).*—Lanceolate.
- *Shape of apex.*—Pointed.
- *Shape of base.*—Pointed.
- *Texture.*—Smooth.
- *Aspect.*—Horizontal.
- *Margin type.*—Serrated.
- *Color.*—Young leaves: Upper surface: 137A. Lower surface: 137C. Mature leaves: Upper surface: 136A. Lower surface: 137C.
- *Petiole.*—Not present, leaves are directly connected to the stem.
- *Veins.*—Venation type: Pinnate. Color: Upper surface: 137A. Lower surface: 144C.

FLOWER

Natural flowering season at specified location(s): In Middle Europe, outdoors from middle of May until frost.

Flower type and habit: 1 flower per leaf axil.
Number of flowers per plant: Plenty.
Bud (described when the tips of the petals are visible):
*Shape.*—Globose.
*Diameter.*—5 mm.
*Length.*—5 mm.
*Color.*—139B.
Flower:
*Shape.*—5 petals, basal fused together ending in a pharynx.
*Diameter.*—30 mm.
*Length.*—30 mm.
*Depth.*—1.0 cm.
*Petal length.*—10 mm.
*Petal width.*—15 mm.
*Petal apex shape.*—Round.
*Petal margin.*—Smooth, undulating.
*Texture.*—Smooth, velvety.
*Color.*—When opening: Upper surface: Upper petals 87A, lower petals 87B fading to a whitish, more white than 97D, edge. Lower surface: Upper petals 87B, lower petals 87C fading to a whitish, more white than 97D, edge. Fully opened: Upper surface: Upper petals 87A, lower petals 87B fading to a whitish, more white than 97D, edge. Lower surface: Upper petals 87B, lower petals 87C fading to a whitish, more white than 97D, edge.
Sepal:
*Number.*—5.
*Length.*—5 mm.
*Width.*—3 mm.
*Shape.*—Between lanceolate and elliptic.
*Apex.*—Pointed.
*Base.*—Fused.
*Margin.*—Entire.
*Color.*—139B (Both surfaces).
Peduncle:
*Length.*—3 cm.
*Diameter.*—1 mm.
*Color.*—144A.
*Orientation.*—Angled 45° upright.
*Strength.*—Elastic.
Pedicel: Absent.
Disease resistance: None observed at this time.
Fragrance: Absent.
Weather tolerance: Susceptible to cold temperatures.
Lastingness of the bloom: About 20 days on the plant.
Seed production and description: Light brown, very small (approximately 0.13 g/1000 seeds).
Fruit production and description: Rarely observed. When present, they are green capsules with approximately 50 seeds per capsula. When seeds are brown and dry clasping they measure in diameter approximately 0.5 cm.

REPRODUCTIVE ORGANS

Stamens:
*Number* (*per flower*).—4.
*Filament length.*—2 mm.
*Anthers.*—Shape: Short tube. Length: 5 mm. Color: White.
*Pollen.*—Color: White. Amount: Plentiful.
Pistils:
*Length.*—5 mm.
*Style.*—Length: 3 mm. Color: White.
*Ovaries.*—Length: 1.5 mm. Color: Dark brown.
*Stigma.*—Shape: Pointed. Color: White.

I claim:

1. A new and distinct variety of *Angelonia* plant substantially as shown and described.

* * * * *